(12) United States Patent
Pich

(10) Patent No.: US 12,702,432 B2
(45) Date of Patent: Aug. 11, 2026

(54) CATHETER DEVICES WITH DAMPING ASSEMBLIES FOR CORE WIRES

(71) Applicant: Bard Peripheral Vascular, Inc., Franklin Lakes, NJ (US)

(72) Inventor: John Pich, Chandler, AZ (US)

(73) Assignee: BARD PERIPHERAL VASCULAR, INC., Franklin Lakes, NJ (US)

( * ) Notice: Subject to any disclaimer, the term of this patent is extended or adjusted under 35 U.S.C. 154(b) by 113 days.

(21) Appl. No.: 18/720,983

(22) PCT Filed: Dec. 22, 2021

(86) PCT No.: PCT/US2021/064854
§ 371 (c)(1),
(2) Date: Jun. 17, 2024

(87) PCT Pub. No.: WO2023/121664
PCT Pub. Date: Jun. 29, 2023

(65) Prior Publication Data

US 2025/0057553 A1 Feb. 20, 2025

(51) Int. Cl.
*A61B 17/22* (2006.01)
*A61B 17/00* (2006.01)

(52) U.S. Cl.
CPC .................. *A61B 17/22012* (2013.01); *A61B 2017/00526* (2013.01); *A61B 2017/22014* (2013.01); *A61B 2017/22038* (2013.01)

(58) Field of Classification Search
CPC ........ A61B 17/22004; A61B 17/22031; A61B 17/22012; A61B 17/221; A61B 17/225;
(Continued)

(56) References Cited

U.S. PATENT DOCUMENTS 4,676,530 A * 6/1987 Nordgren ........... A61M 39/1011 411/521
5,382,228 A * 1/1995 Nita ................ A61B 17/22012 601/3
(Continued)

FOREIGN PATENT DOCUMENTS

EP 2036620 B1 4/2015
WO 2004075945 A2 9/2004
(Continued)

OTHER PUBLICATIONS

International Search Report & Written Opinion dated Aug. 8, 2022 related to PCT/US21/64854.

*Primary Examiner* — Kankindi Rwego
(74) *Attorney, Agent, or Firm* — DINSMORE & SHOHL LLP

(57) ABSTRACT

A damping assembly for a core wire of an ultrasonic catheter assembly includes a body for receiving the core wire. The body includes a bore extending from a proximal end of the body. The bore is defined by an interior surface of the body and includes an insertion region at the proximal end and a compression region disposed distal to the insertion region. A plurality of compression members are disposed within the compression region of the bore. A retention member extends at least partially into the compression region to axially compress the plurality of compression members. The interior surface of the body defining the insertion region of the bore corresponds in shape to at least a portion of an exterior surface of the retention member to facilitate insertion of the retention member into the bore.

17 Claims, 7 Drawing Sheets

(58) Field of Classification Search

CPC .. A61B 2017/00526; A61B 2017/2004; A61B 2017/22014; A61B 2017/22015; A61B 2017/22038; A61M 39/1011; A61M 2039/0229; A61M 2039/1027

USPC .................................................. 606/127, 128

See application file for complete search history.

(56) References Cited

U.S. PATENT DOCUMENTS

| | | | | |
|---|---|---|---|---|
| 5,916,192 A * | 6/1999 | Nita | A61B 18/245 | 604/509 |
| 2007/0249197 A1* | 10/2007 | Spranger | F16L 41/02 | 439/152 |
| 2013/0023897 A1* | 1/2013 | Wallace | A61B 17/22004 | 606/128 |
| 2018/0132875 A1* | 5/2018 | Singh | A61B 17/320068 | |
| 2022/0395285 A1* | 12/2022 | Dolan | A61B 17/22012 | |

FOREIGN PATENT DOCUMENTS

| | | |
|---|---|---|
| WO | 2018013629 A1 | 1/2018 |
| WO | 2018097856 A1 | 5/2018 |

* cited by examiner

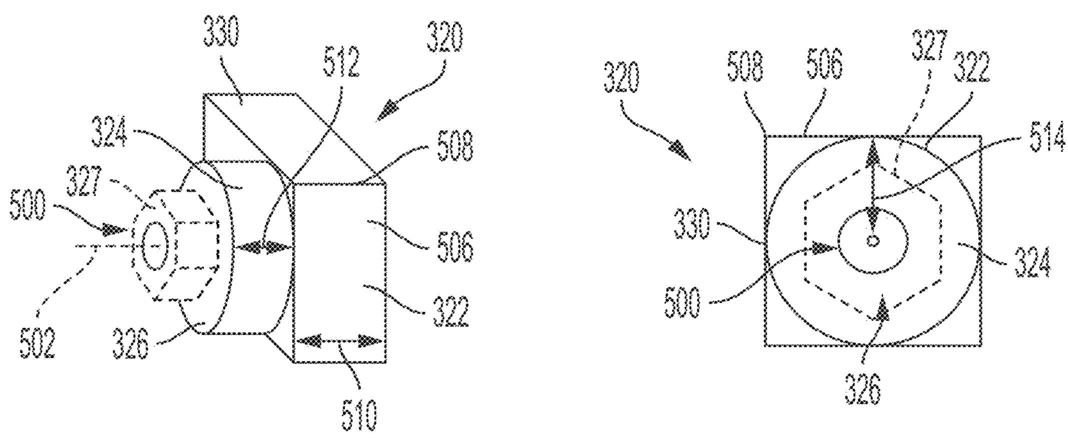
FIG. 5A
FIG. 5B
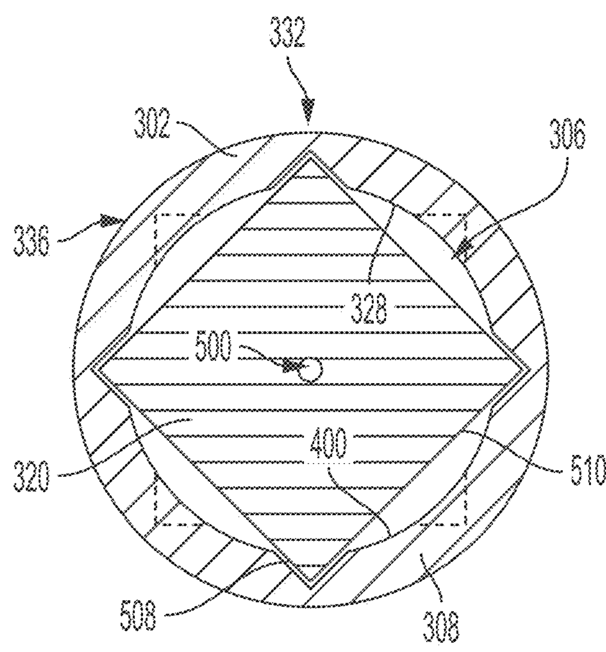
FIG. 5C

CATHETER DEVICES WITH DAMPING ASSEMBLIES FOR CORE WIRES

CROSS-REFERENCE TO RELATED APPLICATIONS

This application is a U.S. national phase of International Application No. PCT/US21/64854, filed Dec. 22, 2021, which is incorporated herein by reference in its entirety.

The present specification generally relates to damping assemblies for ultrasonic systems used in surgical procedures such as for atherosclerosis.

BACKGROUND

Atherosclerosis is characterized by one or more intravascular lesions formed at least partially of plaque, which may also include blood-borne substances such as fat, cholesterol, and calcium. An intravascular lesion such as an arterial lesion can form on a wall of an arterial lumen and build out across the lumen to an opposite wall thereof. Surgical procedures for atherosclerosis such as angioplasty or atherectomy can be used to restore patency and blood flow lost to the one or more intravascular lesions. Ultrasonic systems or devices may be used to ablate or remove obstructive material from blood vessels. Such systems may include a core wire communicatively coupled to an ultrasonic transducer. The core wire may be delivered to the location of the obstructive material and deliver ultrasonic energy to the obstructive material to break up the obstructive material and restore blood flow. However, the ultrasonic energy may result in vibrations and structural fatigue of the core wire.

Accordingly, a need exists for damping assemblies to improve performance of such ultrasonic systems.

SUMMARY

Embodiments of the present disclosure are directed to improvements over the above limitations by providing damping assemblies for use in ultrasonic systems that include a plurality of compression members that are compressed around a core wire using a retention member that is received in a bore that is shaped to receive and hold the retention member in a desired orientation. The combination of the shaped bore and the retention member described herein facilitates consistent installation and compression of the compression members by the retention member, thereby providing a desired amount of damping of transverse oscillations of the core wire.

According to one embodiment of the present disclosure, a damping assembly for a core wire of an ultrasonic catheter assembly includes a body for receiving the core wire. The body includes a bore extending from a proximal end of the body. The bore is defined by an interior surface of the body and includes an insertion region at the proximal end and a compression region disposed distal to the insertion region. A plurality of compression members are disposed within the compression region of the bore. A retention member extends at least partially into the compression region to axially compress the plurality of compression members. The interior surface of the body defining the insertion region of the bore corresponds in shape to at least a portion of an exterior surface of the retention member to facilitate insertion of the retention member into the bore.

According to another embodiment of the present disclosure, a system for modifying intravascular lesions includes an ultrasonic generator configured to generate an electric signal, an ultrasonic transducer communicatively coupled to the ultrasonic generator to receive the electric signal and generate vibrational energy, and a catheter assembly. The catheter assembly includes an ultrasonic connector coupling a core wire to the ultrasonic transducer to receive the vibrational energy therefrom and a damping assembly. The damping assembly includes a body receiving the core wire, the body comprising a bore defined by an interior surface of the body. The bore incudes an insertion region at a proximal end of the body and a compression region disposed distal to the insertion region. The damping assembly also includes a plurality of compression members disposed within the compression region of the bore. The damping assembly also includes a retention member extending at least partially into the compression region to radially compress the plurality of compression members. The interior surface of the body defining the insertion region of the bore corresponds in shape to at least a portion of an exterior surface of the retention member to facilitate insertion of the retention member into the bore.

According to another embodiment of the present disclosure, a method for making a catheter assembly for modifying intravascular lesions includes fabricating a body of a damping assembly including a bore, disposing a core wire through the bore, disposing a plurality of compression members in the bore around the core wire; and inserting a retention member into the bore by aligning one or more exterior surface components of the retention member with one or more insertion features of the bore and compressing the plurality of compression members with the retention member such that the plurality of compression members damp vibrational energy in the core wire.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 5A schematically depicts a perspective view of a retention member of the damping assembly of FIGS. 3A and 3B, according to one or more embodiments described herein;

FIG. 5B schematically depicts a view of a distal end of the retention member of FIG. 5A, according to one or more embodiments described herein;

FIG. 5C schematically depicts a cross-sectional view of the retention member of FIGS. 5A and 5B when inserted into the body of FIGS. 4A and 4B, through the line 5C-5C of FIG. 4B, according to one or more embodiments described herein.

DETAILED DESCRIPTION

Figure 1:
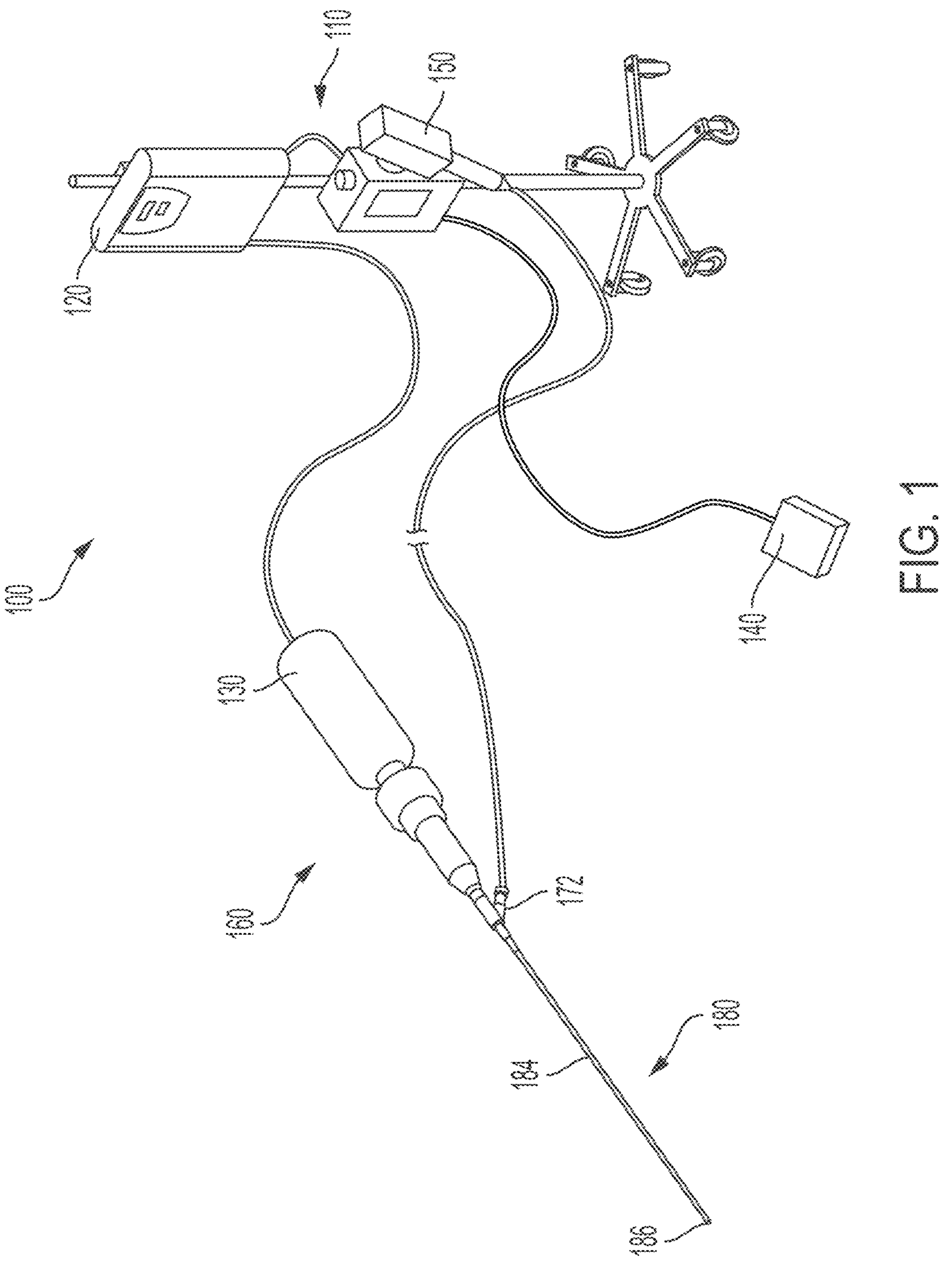
FIG. 1 schematically depicts a system including an ultrasonic generator configured to provide ultrasonic energy down a core wire to a region of interest, according to one or more embodiments described herein.

Embodiments of the present disclosure are directed a damping assembly for damping vibrations of a core wire of an ultrasonic catheter assembly. The damping assembly includes a body for receiving the core wire. The body defines a bore extending from a proximal end of the body. The bore is defined by an interior surface of the body and comprises an insertion region at the proximal end and a compression region disposed distal to the insertion region. A plurality of compression members (e.g., O-rings, elastomeric material, or the like) are disposed within the compression region of the bore. A retention member extends at least partially into the compression region to axially compress the plurality of compression members. The interior surface of the body defining the insertion region of the bore corresponds in shape to at least a portion of an exterior surface of the retention member to facilitate insertion of the retention member into the bore. The axial compression of the plurality of compression members by the retention member may lead to a radial compression of the plurality of compression members via the interior surface forming the compression region. Such radial compression of the plurality of compression members may damp energy of certain vibrational modes for the core wire. For example, the plurality of compression members may damp vibrations of the core wire in a direction perpendicular to the axis of the core wire (e.g., transverse vibration modes) such that a greater portion of ultrasonic energy vibrates in a longitudinal mode that is used to modify or break up obstructive material in a vessel. The amount of damping provided by the plurality of compression members may be dependent on the extent of axial compression by the retention member, as well as the alignment of the retention member. The damping assemblies of the present disclosure are structured to facilitate consistent alignment and placement of the retention member, thereby providing predictable and consistent performance.

In embodiments, the corresponding surface shapes of the retention member and the interior surface of the body beneficially facilitate alignment of the retention member along a desired direction of compression. Such alignment may facilitate a uniform compression of the plurality of compression members, aiding in consistency of performance. In embodiments, the interior surface of the bore defining the insertion region comprises one or more insertion features that correspond in shape to surface components (e.g., corners, grooves, bumps, protrusions, cavities, and the like) of the exterior surface of the retention member to facilitate insertion and retention of the retention member within the bore. For example, in embodiments, the insertion features may correspond in shape to a plurality of corners on the exterior surface of the retention member. To insert the retention member into the bore via the insertion region, the corners of the retention member may be aligned (e.g., rotationally aligned) with the insertion features, allowing the retention member to be pressed into the bore. In embodiments, ends of the insertion features stop insertion of the retention member at a desired position to provide a desired amount of compression of the compression members.

In embodiments, the bore comprises a rotation region extending between the insertion region and the compression region. The rotation region may be sized to receive the retention member so that the retention member may be rotated such that the surface features thereof are out of alignment with the insertion features of the insertion region of the bore. This way, axial compression via the plurality of compression members does not result in the retention member being forced proximally out of the bore. In embodiments, the interior surface of the body defining the bore comprises one or more locking features, such as a plurality of locking features. In embodiments, the locking features may be., channels, grooves, cavities, and the like. In embodiments, the one or more locking features are shaped to correspond to the plurality of surface features of the retention member. Via the rotation region, the retention member may be rotated such that the plurality of locking features are aligned with the plurality of surface features, such that expansion of the compression members pushes the retention member proximally until a proximal end of the retention member contacts ends of the plurality of locking features. This way, lengths of the plurality of locking features may be selected to achieve a desired amount of compression of the plurality of compression members, thereby providing a desired amount of damping to the vibrations of the core wire.

These and additional features and embodiments will be described in greater detail herein.

FIG. 1 schematically depicts a system 100 according to an example embodiment of the present disclosure. The system 100 may generally include a console 110 coupled to a catheter assembly 160 generally configured for modifying intravascular lesions including crossing the intravascular lesions, ablating the intravascular lesions, or a combination of crossing and ablating the intravascular lesions. It should be understood that the system 100 is only an example and the damping assemblies described herein may be implemented in other ultrasonic catheter systems.

In embodiments, the console 110 is used to monitor and control various components (e.g., the catheter assembly 160) of the system 100. For example, the console 110 may include a computing system providing a user interface through which a system operator monitors and controls operation of the catheter assembly 160. In embodiments, the system 100 includes an ultrasonic energy-producing mechanism including an ultrasonic generator 120 and an ultrasonic transducer 130 that together deliver ultrasonic vibrations through the catheter assembly 160. In embodiments, the console 110 includes the ultrasonic generator 120, the catheter assembly 160 includes the ultrasonic transducer 130, and the ultrasonic energy-producing mechanism is distributed between the console 110 and the catheter assembly 160. The ultrasonic energy-producing mechanism is configured to convert electrical energy into vibrational energy. For example, the ultrasonic generator 120 is configured to convert an alternating electric current signal (e.g., from a power grid) into a high-frequency current (e.g., a current with a frequency commensurate with the operating frequency of the ultrasonic transducer 130), and the ultrasonic transducer 130, in turn, is configured to convert the high frequency current produced via the ultrasonic generator 120 into vibrational energy at a particular vibrational frequency (e.g., greater than or equal to 15 kHz and less than or equal to 25 kHz).

In embodiments, the console 110 includes a foot switch 140 configured to activate and deactivate the system 100 such as activate and deactivate at least the ultrasonic energy-producing mechanism (e.g., the ultrasonic generator 120 and/or the ultrasonic transducer 130) and any components thereof or any components coupled thereto. When the system 100 is powered, the foot switch 140 may be used to activate or deactivate the system 100, thereby activating or deactivating components of the ultrasonic energy-producing mechanism such as the ultrasonic transducer 130; components coupled to the ultrasonic energy-producing mechanism, such as a core wire 184 and a tip or tip member 186 of the core wire 184 (see FIG. 2); or combinations thereof.

In embodiments, the console 110 includes an injector 150 configured to inject an irrigant into an irrigation port 172 of the catheter assembly 160. The irrigant includes, for example, a sterile liquid (e.g., water, saline, heparinized saline, etc.) for irrigating an anatomical area undergoing an intravascular-lesion-modifying procedure (e.g., crossing an intravascular lesion, ablating an intravascular lesion, etc.), and for cooling the core wire 184. For example, the liquid provided to the anatomical area via the injector 150 and irrigation port 172 may be used to cool various components of the catheter assembly 160 (e.g., a core wire, a wire tip, etc.). In embodiments, the foot switch 140 can be further configured to activate and deactivate the injector 150 when the system 100 is respectively activated and deactivated with the foot switch 140.

The catheter assembly 160 includes a catheter body 180. As described herein, the catheter body 180 may include a core wire 184 that is provided to an intravascular legion. Ultrasonic energy is generated via the ultrasonic generator 120 and ultrasonic transducer 130, coupled into the core wire 184, and thereby guided to the intravascular legion. The ultrasonic energy propagates to a tip member 186 where it is transmitted to the intravascular legion for treatment. As noted above, it is beneficial to damp unwanted vibrations of the core wire 184 of the catheter body 180 (e.g., along directions extending perpendicular to an axis of the core core), while still permitting longitudinal adjustment of the tip member 186 relative to other components of the catheter body 180 (e.g., a sheath of the catheter).

Figure 2:
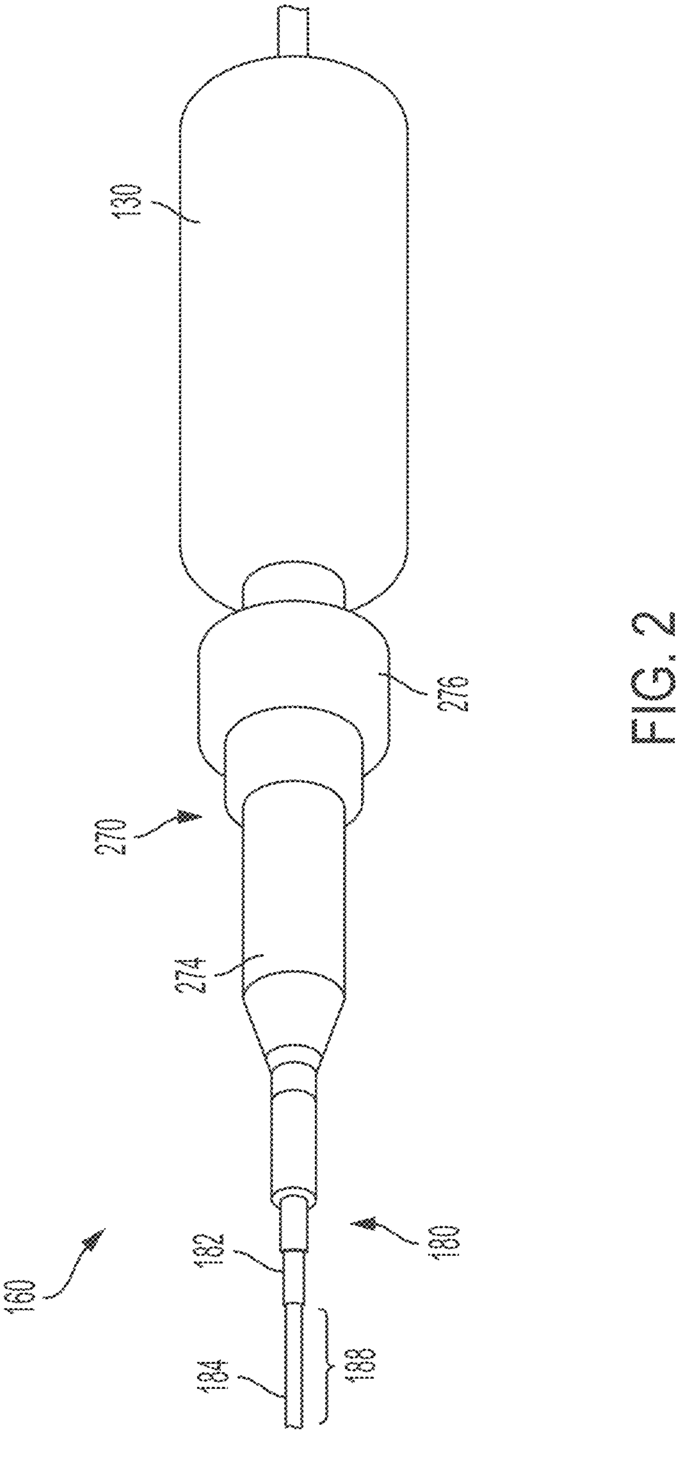
FIG. 2 schematically depicts a catheter assembly of the system of FIG. 1, according to one or more embodiments described herein.

With reference now to FIG. 2, the catheter assembly 160 of the system 100 of FIG. 1 is depicted in greater detail. The catheter assembly 160 includes a housing 270 coupled to the catheter body 180. In embodiments, the catheter body 180 includes a sheath 182, a core wire 184 disposed in a lumen of the sheath 182, and the tip or tip member 186 (see FIG. 1). The catheter assembly 160 may be configured for modifying intravascular lesions including crossing the intravascular lesions, ablating the intravascular lesions, or a combination of crossing or ablating the intravascular lesions via the tip member 186. As shown in FIG. 2, the housing 270 may include a hub 274 and a lock collar 276 for locking the housing 270 onto the ultrasonic transducer 130. In embodiments, the lock collar 276 is attached to the housing 270 via a threaded connection or other suitable fastening method (e.g., adhesive, magnetic coupling). Locking the housing 270 onto the ultrasonic transducer 130 may ensure a proximal end of the core wire 184 is vibrationally coupled to the ultrasonic transducer 130 for modifying intravascular lesions.

Figure 3A:
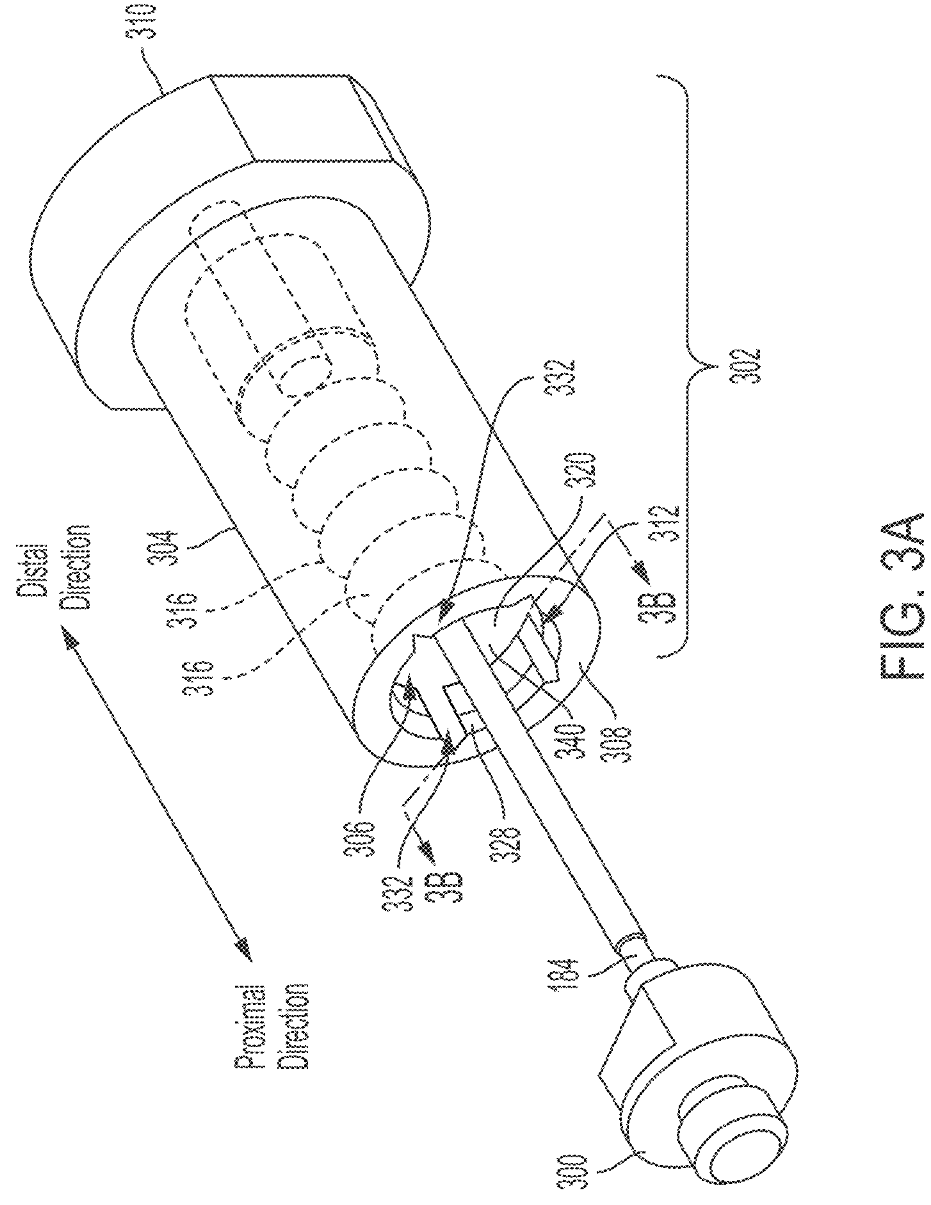
FIG. 3A schematically depicts a perspective view of a damping assembly of the catheter assembly of FIG. 2, according to one or more embodiments described herein.
Figure 3B:
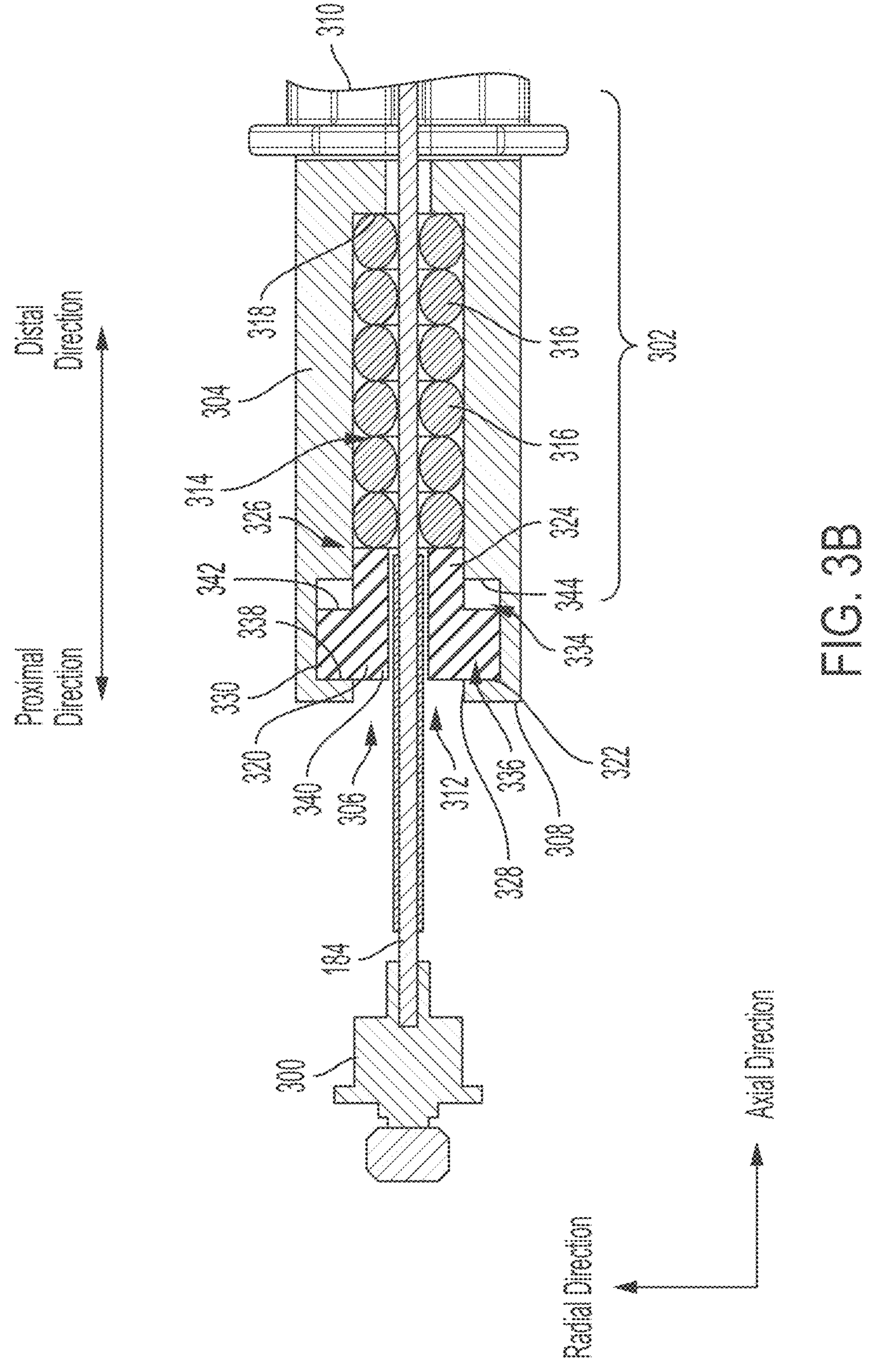
FIG. 3B schematically depicts a cross-sectional view of the damping assembly through the line 3B-3B of FIG. 3A, according to one or more embodiments described herein.

Referring collectively to FIGS. 3A and 3B, a proximal end of the core wire 184 is vibrationally coupled to the ultrasonic transducer 130 by an ultrasonic connector 300 (e.g., through an intervening ultrasonic horn). For example, the ultrasonic connector 300 may be disposed between a proximal end of the hub 274 and a distal end of the ultrasonic transducer 130. In embodiments, a distal end of the core wire 184 is vibrationally coupled to the tip member 186 (see FIG. 1). As such, the ultrasonic connector 300 is configured to impart or otherwise transfer the vibrational energy from the ultrasonic transducer 130 to the core wire 184. The core wire 184 is configured to impart or otherwise transfer the vibrational energy to the tip or tip member 186 (see FIG. 1) of the core wire 184 for modifying intravascular lesions.

As depicted in FIG. 2, a length 188 of the core wire 184 may extend distally beyond the sheath 182 of the catheter assembly 160. Alternatively, in some embodiments, sheath 182 may extend along an entire length of core wire 184. In some embodiments, a tip (such as, but not limited to, a metallic tip) may be attached to both the distal end of sheath 182 and to the distal end of core wire 184. Ultrasonic energy generated by the ultrasonic transducer 130 may cause vibrational displacement of the core wire 184 extending distally beyond the sheath 182 (e.g., in a transverse direction perpendicular to the core wire 184 or a longitudinal direction perpendicular to the core wire 184). Such vibrational displacement may be used to apply forces to modify intravascular lesions disposed within a blood vessel. In embodiments, the ultrasonic transducer 130 may generate ultrasonic waves propagating through the core wire 184 within a frequency range including about 20 kHz (e.g., between 15 kHz and 25 kHz, or between about 19 kHz and about 21 kHz) to cause both longitudinal and transverse displacement of the core wire 184 extending distally beyond the sheath 182. The longitudinal displacement may be used to cross or penetrate intravascular legions, whereas transverse displacement may be used to ablate or break up the intravascular legions.

FIGS. 3A and 3B schematically depict a damping assembly 302 for damping transverse vibrations of the core wire 184 at a proximal end of the core wire 184, according to some embodiments. The damping assembly 302 is depicted to include a body 304. In embodiments, the body 304 may be coupled to, integral with, or otherwise positioned within the housing 270 described herein with respect to FIG. 2. For example, in embodiments, the body 304 may be integral with the hub 274 (see FIG. 2) and extend distally from the ultrasonic connector 300. The damping assembly 302 may be positioned proximate a vibration node of the core wire 184 and be configured to damp transverse vibrations of the core wire 184 to provide a desired vibrational profile of the core wire 184 at the tip member 186 (see FIG. 1) for modifying intravascular legions. In particular, the damping assembly 302 may prevent vibrational energy from being transferred to body 304 and keeps energy focused at the tip member 186 (depicted in FIG. 1).

Referring to FIG. 3B, the body 304 of the damping assembly 302 is depicted to include a bore 306 extending therethrough from a proximal end 308 to a distal end 310 thereof. The core wire 184 may extend through from the ultrasonic connector 300 and through the bore 306. The bore 306 includes an insertion region 312 and a compression region 314. A plurality of compression members 316 (e.g., O-rings) are inserted into the compression region 314 of the bore 306. In embodiments, the plurality of compression members 316 may include 2 to 12 O-rings (e.g., 4 O-rings, 5 O-rings, 6 O-rings, 7 O-rings). The plurality of compression members 316 are compressed in the compression region 314 of the bore 306 between a distal end 318 of the bore 306 and a retention member 320. As depicted, the core wire 184 may extend through the plurality of compression members 316 such that the plurality of compression members 316 circumferentially surround the core wire 184.

The retention member 320 may be retained within the bore 306 via the structures described in greater detail herein to axially compress the plurality of compression members 316 within the compression region 314. Axial compression of the plurality of compression members 316 by the retention member 320 may result in radial compression of the core wire 184 via the plurality of compression members 316 (e.g., the plurality of compression members 316 may radially deform as a result of the axial compression to compress the core wire 184). Such radial compression may damp transverse vibrations of the core wire 184 induced by ultrasonic energy from the ultrasonic transducer 130 in favor of longitudinal vibrations, thereby facilitating the core wire 184 crossing or penetrating intravascular legions. In embodiments, a geometric center of the bore 306 is axially aligned with a vibration node of the core wire 184, where the core wire 184 minimally vibrates in the transverse direction, to minimize friction-induced heating caused by damping.

In embodiments, the insertion region 312 of the bore 306 is shaped to receive the retention member 320 and to position the retention member 320 relative to the plurality of compression members 316 so as to provide a desired amount and/or distribution of compression thereto. In embodiments, and as depicted in FIG. 3A, an interior surface 328 of the body 304 defining the bore 306 corresponds in shape to at least a portion of an exterior surface 330 of the retention member 320 to facilitate alignment thereof. In embodiments, the interior surface 328 defines one or more insertion features 332, such as a plurality of insertion features. In embodiments, the one or more insertion features can be grooves, channels, cavities, and the like that are shaped to receive surface features (e.g., corners, edges, protrusions, etc.) of the retention member 320. Alignment of the plurality of insertion features 332 and the surface features of the retention member 320 (e.g. disposed on the exterior surface 330 thereof) may facilitate pressing the retention member 320 through the insertion region 312, such that the retention member 320 at least partially extends into the compression region 314 to mechanically contact the plurality of compression members 316. As shown in FIG. 3B, the retention member 320 may include a distal end 326 that is disposed within the compression region 314 and compresses the plurality of compression members 316 therein.

A distance (e.g., in the axial direction) between the distal end 326 of the retention member 320 and the distal end 318 of the compression region 314 may determine an extent of the compression of the plurality of compression members 316. In embodiments, the positioning of the distal end 326 is determined at least partially from the structure of the retention member 320. As depicted in FIG. 3B, the retention member 320 may include a first portion 322 and a second portion 324 that extends distally from the first portion 322. In embodiments, the first portion 322 and the second portion 324 include different cross-sectional shapes (e.g., differ from one another in at least one of a cross-sectional size, a cross-sectional geometry, or the like). In embodiments, the second portion 324 may be sized and shaped to correspond to a cross-sectional shape of the compression region 314 of the bore 306, so as to be positionable within the compression region 314. For example, in embodiments, the second portion 324 comprises a substantially cylindrical-shaped peg having a diameter corresponding to that of the compression region 314. The second portion 324 may compress the plurality of compression members 316 by an amount that is at least partially determined by an axial extent (e.g., length) thereof. Such a multi-portion geometry of the retention member 320 may facilitate holding the retention member 320 at a desired position within the bore 306 via the exterior surface 330, as described herein.

Referring still to FIG. 3B, in embodiments, the first portion 322 of the retention member 320 is inserted into the insertion region 312 of the bore 306 via the plurality of insertion features 332. For example, in the depicted embodiment, the first portion 322 includes a substantially block-shaped member 340 (see FIGS. 5A and 5B) and the plurality of insertion features 332 are shaped to receive the corners of the substantially block-shaped member 340. By receiving the corners of the substantially block-shaped member 340, the plurality of insertion features 332 ensure that the retention member 320 is pressed into the bore 306 in a direction parallel to the core wire 184 (e.g., in the axial direction) to facilitate uniform compression of the plurality of compression members 316. In embodiments, once positioned in alignment with the bore 306 (e.g., such that the corners of the first portion 322 are aligned with the plurality of insertion features 332), the retention member 320 may be pressed into the bore 306 until an end 342 of the first portion 322 contacts a stopping surface 344 delineating a distal boundary of the insertion region 312.

As depicted in FIG. 3B, in embodiments, the bore 306 includes a rotation region 334 extending between the insertion region 312 and the compression region 314. In embodiments, within the rotation region 334, the bore 306 is sized and shaped to allow rotation of the first portion 322 of the retention member 320 around the core wire 184 such that the corners of the first portion 322 are rotated out of alignment with the plurality of insertion features 332 (see FIG. 3A). As a result, when the retention member 320 is released from application of external forces during insertion into the bore 306, elastic forces from the plurality of compression members 316 do not push the retention member 320 out of the bore 306. For example, when the retention member 320 is inserted into the bore 306, an axial pushing force may be applied to the first portion 322 until the second portion 324 at least partially extends into the compression region 314 of the bore 306 and the corners of the first portion 322 are entirely disposed in the rotation region 334. The retention member 320 may then be rotated such that the corners are out of alignment with the plurality of insertion features 332 and the axial pushing force may then be released, resulting in the plurality of compression members 316 applying a compressive force to the retention member 320 in the proximal direction. The misalignment between the corners of the first portion 322 and the plurality of insertion features 332 facilitates retention of the retention member 320 within the bore 306.

Figure 4A:
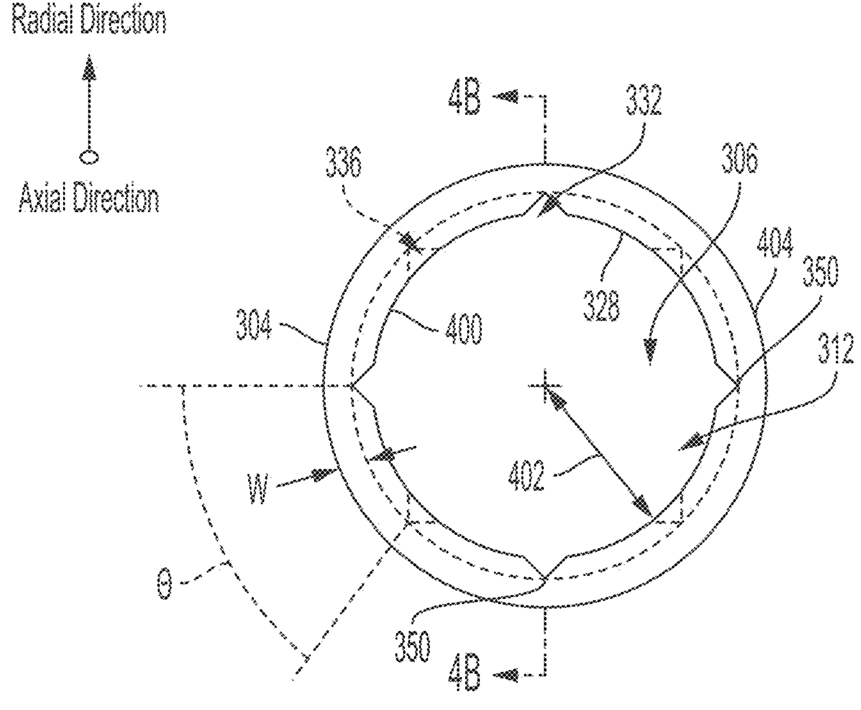
FIG. 4A schematically depicts a view of a proximal end of a body of the damping assembly of FIGS. 3A and 3B, according to one or more embodiments described herein.

As depicted in FIGS. 3B and 4A, in embodiments, the interior surface 328 defining the bore 306 includes a plurality of locking features 336. Each of the plurality of locking features 336 may extend from the rotation region 334 of the bore 306 to a retention surface 338 disposed distally to the proximal end 308 of the body 304. In embodiments, the plurality of locking features 336 are substantially similar in shape to the plurality of insertion features 332 within the insertion region 312. The plurality of locking features 336 may include a plurality of grooves shaped to receive the plurality of corners of the first portion 322 of the retention member 320 after the retention member 320 is rotated. As a result, the force applied via the plurality of compression members 316 may compress the first portion 322 against the retention surface 338 of each of the plurality of locking features 336. As such, the lengths of the plurality of locking features 336 may be used to determine an amount of retained compression in the plurality of compression members 316, thereby determining an amount of radial compression applied to the core wire 184. In embodiments, the length (e.g., corresponding to the axial length 412 depicted in FIG. 4B) of the plurality of locking features 336 is determined based on the number of compression members 316 in the plurality of compression members 316 and the diameter of the core wire 184. In embodiments, the length of the plurality of locking features 336 is greater than or equal to 1.0 mm and less than or equal to 5.0 mm (e.g., 2.0 mm, 3.0 mm, 4.0 mm). Such a range may facilitate adequate damping of transverse vibrations of the core wire 184 while allowing linear actuation of the core wire 184 through the damping assembly 302.

The plurality of insertion features 332 and the plurality of locking features 336 defined by the interior surface 328 beneficially provide precise control over both the alignment of the retention member 320 during its insertion into the bore 306, as well as the amount of retained compression within the plurality of compression members 316. The correspondence in shape between the interior surface 328 (e.g., at the plurality of locking features 336) and the exterior surface 330 of the retention member 320 also prevents rotation and movement of the retention member 320 during operation of the system 100 (see FIG. 1). Such an embodiment may provide improved performance over a threaded retention member (e.g., where the interior surface 328 includes threads that engage with threads disposed on the exterior surface 330 of the retention member 320), where vibration of the core wire 184 may cause rotation of the retention member 320 and potential changes in position, requiring periodic tightening of such a threaded retention member. The damping assembly 302 may also beneficially avoid the need for additional components (e.g., locking pins and the like) to fix the position of the retention member 320, facilitating compactness and improved performance.

Figure 4B:
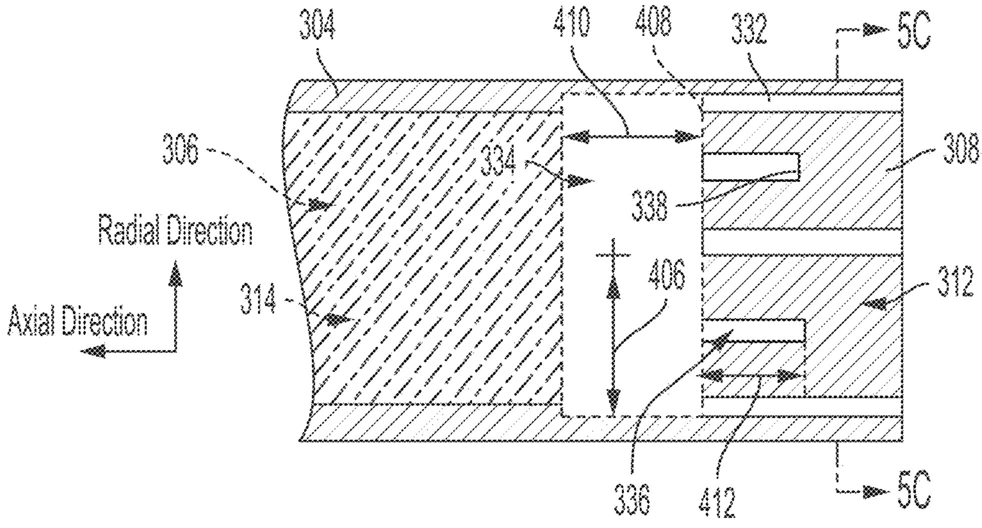
FIG. 4B schematically depicts a cross-sectional view of the body through the line 4B-4B of FIG. 4A, according to one or more embodiments described herein.

FIGS. 4A and 4B schematically depict various aspects of the body 304 and bore 306 of the damping assembly 302 described herein with respect to FIGS. 3A and 3B, according to an example embodiment. As shown in FIG. 4A, the body 304 at the insertion region 312 of the bore 306 may include a cylindrical body portion 400 that is substantially cylindrically-shaped and include an inner radius 402 that is greater than or equal to a radial dimension of the second portion 324 of the retention member 320 configured to be inserted therein (see FIGS. 3A and 3B). The plurality of insertion features 332 may include a plurality of channels extending radially outward from the interior surface 328 of the body 304 and be shaped to receive a plurality of surface features of the exterior surface 330 of the retention member 320 (see FIGS. 3A and 3B). The plurality of insertion features 332 may be angularly distributed throughout a circumference of the interior surface 328 in a manner that corresponds to a distribution of the surface features on the exterior surface 330 of the retention member 320 such that the plurality of insertion features 332 correspond to a peripheral shape of at least a portion of the retention member 320.

In embodiments, a thickness of the body 304 may be selected such that a minimum wall thickness W separates an exterior surface 404 of the body 304 from ends 350 of the plurality of insertion features 332. The minimum wall thickness W may be selected based on the material out of which the body 304 is constructed so that the body 304 retains sufficient structural strength to hold the retention member 320 (see FIGS. 3A and 3B) in a desired compression position. In embodiments, body 304 may be made from any suitable material, such as, but not limited to, polycarbonates, acrylics, or the like. In some embodiments, the wall thickness W of the body 304 may be increased through a proximal portion of the housing for support of the plurality of insertion features. In such embodiments, the wall thickness of an outer diameter of the body 304 may be increased through the proximal portion to substantially correspond to a wall thickness in the distal portion.

As indicated by the dashed lines depicted in FIG. 4A, the plurality of locking features 336 correspond in cross-sectional shape to the plurality of insertion features 332. As shown, corresponding ones of the plurality of insertion features 332 and the plurality of locking features 336 are angularly displaced from one another by a rotation angle Θ. The rotation angle Θ may represent the extent that the retention member 320 (see FIGS. 3A and 3B) is rotated once inserted into the bore 306 such that surface features thereof are placed in alignment with the plurality of locking features 336. In embodiments, the rotation angle Θ is approximately 45° (e.g., between 44° and 46°), such that the retention member 320 is rotated by approximately one eighth of a full turn once inserted into the bore 306. Such a rotation angle Θ is beneficial in that the plurality of locking features 336 are disposed between successive ones of the plurality of insertion features 332. In embodiments, the rotation angle Θ may be greater than 0° and less than or equal to 90° (e.g., about) 45°, such that the plurality of insertion features 332 and plurality of locking features 336 are disposed in an alternating circumferential arrangement (e.g., such that at least one of the plurality of locking features 336 is disposed circumferentially between adjacent ones of the plurality of insertion features 332).

As shown in FIG. 4B, the plurality of insertion features 332 may extend an entire axial distance between the proximal end 308 of the body 304 and the rotation region 334. In embodiments, the rotation region 334 of the bore 306 comprises a volume that is greater than that associated with the first portion 322 of the retention member 320 (see FIGS. 3A and 3B) to allow for rotation of the first portion 322 therein once the first portion 322 clears the insertion region 312. In embodiments, the rotation region 334 is substantially cylindrically-shaped and comprises a radius 406 that is greater than or equal to a maximum radial extent of the retention member 320 to permit rotation therein to place the plurality of surface features thereof into alignment with the plurality of locking features 336. In embodiments, the rotation region 334 includes a width 410 (e.g., in the axial direction) that is greater than that associated with a portion (e.g., the first portion 322 depicted in FIGS. 3A and 3B) of the retention member 320.

In embodiments, the plurality of locking features 336 extend from a proximal boundary 408 of the rotation region 334. Each of the plurality of locking features 336 may include an axial length 412 that is designed based on a desired amount of compression for the plurality of compression members 316 (see FIGS. 3A and 3B). After the retention member 320 is inserted into the bore 306 via the insertion region 312 and rotated into alignment with the plurality of locking features 336, the retention member 320 may be released such that the plurality of compression members 316 force the retention member 320 back towards the proximal end 308 until the retention member 320 contacts the retention surface 338 of each of the plurality of locking features 336. Retained compression in the plurality of compression members 316 may hold the retention member 320 in place, resulting in radial compression of the core wire 184.

In the example described with respect to FIGS. 4A and 4B, the insertion region 312, compression region 314, and rotation region 334 of the bore 306 may differ from one another in at least one of radial dimension, geometric shape, and features contained therein. The insertion region 312, for example, may extend along and include each of the cylindrical body portion 400, the plurality of insertion features 332, and the plurality of locking features 336. The rotation region 334 may have an inner radius 402 that is greater than the inner radius 402 of the cylindrical body portion 400 to allow for rotation of the retention member 320 therein. In embodiments, the compression region 314 is substantially cylindrically-shaped and includes a radius that is equal to the inner radius 402 of the cylindrical body portion 400 of the insertion region 312. Boundaries of each of the insertion region 312, compression region 314, and rotation region 334 may be delineated by points of transition between radial dimensions of the bore 306 or ends of the features (e.g., the plurality of insertion features 332, the plurality of locking features 336) therein.

The embodiment described herein with respect to FIGS. 4A and 4B is only an example and it is to be understood that the insertion region 312, compression region 314, and rotation region 334 may have different shapes than those depicted. In embodiments, for example, rather than being angular grooves for receiving corners of a block-shaped retention member, the plurality of insertion features 332 and the plurality of locking features 336 may be semi-cylindrically-shaped grooves for receiving bumps or protrusions formed on the exterior surface 330 of the retention member 320 (see FIGS. 3A and 3B). In embodiments, the plurality of insertion features 332 may be positive features (e.g., bumps, protrusions) configured to be inserted into negative features (e.g., grooves, channels) in the exterior surface 330 of the retention member 320. Embodiments are also envisioned where some of the plurality of insertion features 332 and the plurality of locking features 336 are differently shaped from one another. For example, the plurality of insertion features 332 may be shaped to mechanically interact with differently shaped surface features formed on the exterior surface 330. Embodiments are also envisioned that only include a single insertion feature-locking feature pair. The interior surface 328 may also define a bore 306 that is not cylindrically-shaped. A variety of retention members having a variety of different peripheral shapes may be accommodated within the body 304 via appropriate selection of the bore shape.

FIGS. 5A and 5B schematically depict the retention member 320 of the damping assembly 302 described herein with respect to FIGS. 3A and 3B, according to an example embodiment. The retention member 320 includes a wire bore 500 extending through an entirety thereof along a central axis 502 of the retention member 320. The wire bore 500 is sized greater than a size of the core wire 184 (see FIGS. 3A and 3B) to facilitate insertion of the core wire 184 therethrough. In embodiments, both the first portion 322 and the second portion 324 of the retention member 320 are sections of a monolithic body constructed from a single material. In embodiments, the retention member 320 is formed of a suitable metallic or polymer-based material. In embodiments, for example, the retention member 320 is constructed of a metal such as aluminum, or other material with similar thermal and mechanical properties. In embodiments, the material selected to construct retention member 320 is selected based on mass and density so as not to inhibit operation of the system 100. In embodiments, the first portion 322 and the second portion 324 are formed separately and subsequently attached to one another using a suitable attachment method (e.g., welding, adhesive). In embodiments, the first portion 322 and the second portion 324 are constructed from different materials.

As depicted in FIG. 5A, the first portion 322 of the retention member 320 may be substantially block-shaped and include a plurality of side walls 506 connected to one another via a plurality of corner portions 508. The second portion 324 is a substantially cylindrical shaped peg extending from the first portion 322. In the depicted embodiment, the first portion 322 includes a first axial length 510 and the second portion 324 includes a second axial length 512. In embodiments, the summation first and second axial lengths 510 and 512 is greater than or equal to the summation of the axial length 412 of the plurality of locking features 336 and the width 410 of the rotation region 334 (see FIGS. 4A-4B) such that, after the retention member 320 is disposed in the bore 306, the distal end 326 is disposed in the compression region 314 in contact with the plurality of compression members 316 (see FIGS. 3A-3B). In embodiments, second axial length 512 is greater than first axial length 510, which may provide enhanced stability. In some embodiments, first axial length may be at least 3 mm, though other axial lengths are contemplated and possible based on the particular application.

As depicted in FIG. 5B, the second portion 324 includes a radius 514. In the depicted embodiment, the radius 514 is equal to half a length of one of the plurality of side walls 506 such that the exterior surface 330 smoothly transitions between the first portion 322 and the second portion 324. Such a construction may beneficially aid in inserting the second portion 324 into the compression region 314 of the bore 306 by avoiding stepwise transitions on the exterior surface 330. In embodiments, the radius 514 is less than or equal to an outer radius of the plurality of compression members 316 when compressed inside the compression region 314 of the bore 306 (see FIGS. 3A and 3B). Such a configuration may prevent the plurality of compression members 316 from extending between the exterior surface 330 and the interior surface 328 when compressed by the retention member 320. FIG. 5C schematically depicts a cross-sectional view of the retention member 320 of FIGS. 5A and 5B when being inserted into the bore 306 of the body 304 depicted in FIGS. 4A-4B, according to an example embodiment. In the depicted embodiment, when the retention member 320 is initially inserted into the bore 306, the retention member 320 is aligned such that the corner portions 508 are positioned within the plurality of insertion features 332. The inner radius 402 of the cylindrical body portion 400 (see FIG. 4A) of the insertion region 312 is greater than the radius 514 of the second portion 324 (sec FIG. 5B). When in such a configuration, the corner portions 508 may be the only portion of the retention member 320 that contacts the cylindrical body portion 400. Contact between the corner portions 508 and the plurality of insertion features 332 facilitates alignment between the second portion 324 of the retention member 320 and the compression region 314 of the bore 306 (see FIGS. 3A-3B). The plurality of locking features 336 also contact the corner portion 508 connecting the side walls 506 to retain the retention member 320 in a position where the central axis 502 of the retention member 320 (sec FIG. 5A) extends parallel to the core wire 184 (see FIGS. 3A-3B), resulting in uniform compression of the plurality of compression members 316.

Figure 6:
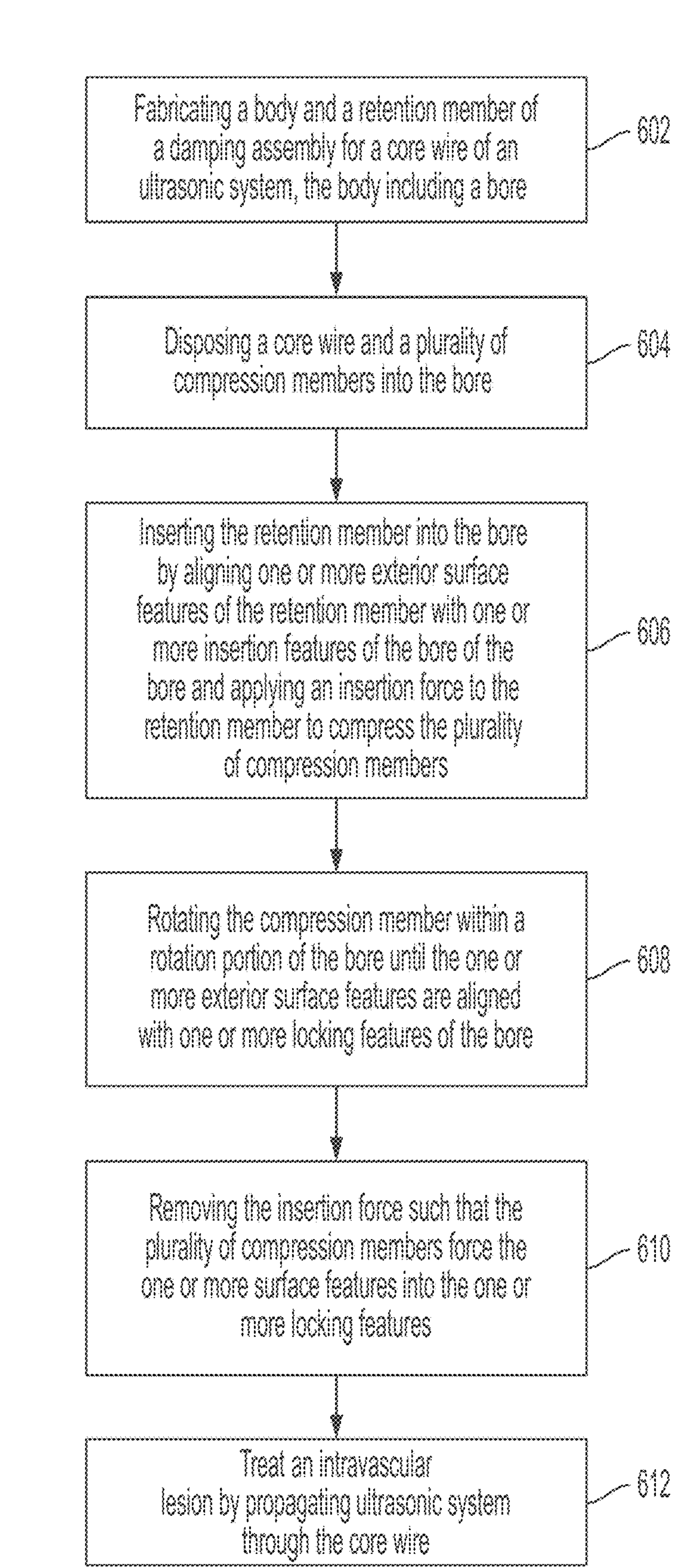
FIG. 6 depicts a flow diagram of a method of fabricating a damping assembly for an ultrasonic system and installing a retention member into a body to compress a plurality of compression members and damp oscillations in a core wire, according to one or more embodiments described herein.

FIG. 6 depicts a flow diagram of a method 600 of fabricating a damping assembly 302 for an ultrasonic system and using the damping assembly 302 to compress a plurality of compression members 316 around a core wire 184 of the ultrasonic system to damp vibrations of the core wire 184. In embodiments, the method 600 may be used to fabricate and use the damping assembly 302 described herein with respect to FIGS. 3A-5C herein to damp vibrational energy of the core wire 184 of the system 100 described herein with respect to FIGS. 1-2. Accordingly, reference will be made to FIGS. 1-5C herein to aid in the description of the method 600. It should be understood that the method 600 may be used to fabricate alternative damping assemblies that are used to damp vibrations in ultrasonic systems other than those depicted in the figures.

At block 602, the body 304 and the retention member 320 of the damping assembly 302 are fabricated. In embodiments, the body 304 is fabricated using a suitable fabrication method to include the bore 306. For example, in embodiments, the body 304 may be formed of a suitable plastic or metallic material and formed via a molding technique. The mold used to form the body 304 may include an inner portion having an exterior surface shaped to correspond to a desired shape of the bore 306 (e.g., to form the insertion region 312, the compression region 314, and the rotation region 334) and an outer portion to form an exterior surface of the body 304. In embodiments, the retention member 320 may be formed using a similar molding technique. In embodiments, the retention member 320 and/or the body 304 are constructed using an additive manufacturing technique (e.g., selective laser sintering, etc.).

At block 604, the core wire 184 and the plurality of compression members 316 are disposed in the bore 306. For example, in embodiments, the core wire 184 may be routed through the body 304, and the plurality of compression members 316 may be disposed around the core wire 184 in the compression region 314 of the bore 306. At block 606, the retention member 320 is inserted into the bore 306 by aligning one or more exterior surface components thereof (e.g., the corner portions 508 depicted in FIGS. 5A-5C) with the plurality of insertion features 332. Once aligned, an insertion force may be applied to the retention member 320 in the axial direction, such that the second portion 324 of the retention member 320 extends into the compression region 314 and compresses the plurality of compression members 316. In embodiments, the retention member 320 is initially forced into the bore 306, such that an entirety of the first portion 322 of the retention member 320 is disposed in the rotation region 334 of the bore 306. For example, the first portion 322 may contact a transition between the rotation region 334 and the compression region 314 to indicate that the retention member 320 has reached as desired position.

At block 608, the retention member 320 is rotated within the rotation region 334 of the bore 306 until the one or more exterior surface components are aligned with the plurality of locking features 336. In embodiments, the retention member 320 is rotated by a predetermined rotation angle Θ (see FIG. 4A) by which the plurality of locking features 336 are angularly offset from the plurality of insertion features 332. In embodiments, the rotation is performed manually by visual observation until alignment between the exterior surface components of the retention member 320 are aligned with the plurality of locking features 336. In embodiments, an actuator is programmed to rotate the retention member 320 by the rotation angle Θ. In embodiments, retention member 320 may include a hex piece 327 (such as a bolt head) as depicted in FIG. 5A and 5B, which may be rotated via the actuator or manually by a user. In such embodiments, the hex piece 327 may include the wire bore 500.

At block 610, the insertion force used to press the retention member 320 into the bore 306 is removed such that the plurality of compression members 316 force the one or more exterior surface components of the retention member 320 into the plurality of locking features 336. Ends of the plurality of locking features 336 may retain the retention member 320 at a desired axial position such that a desired amount of compression is retained in the plurality of compression members 316 to provide a desired amount of damping.

As described herein, an intravascular lesion may be treated in a method of treatment using the assembled ultrasonic system described herein. For example, an intravascular legion may be treated by advancing the core wire 184 into a vessel to a lesion and propagating ultrasonic energy through the core wire 184. For example, an electric signal generated via the ultrasonic generator 120 may be provided to the ultrasonic transducer 130 to generate an ultrasonic vibration (e.g., via operation of the console 110 and/or one or more user input devices (e.g., a foot switch 140, button, knob, or any other user interface device). The core wire 184 may be positioned and advanced within a blood vessel of a patient such that the tip member 186 extends through or proximate to an intravascular legion. The catheter assembly 160 may then be activated to deliver vibrations for engaging and crossing the lesions via activation of the core wire 184. That is, vibration of the tip member 186 is configured to cause the tip member 186 to penetrate intravascular lesions. The damping assembly 302 dampens transverse vibrations and focuses vibrational energy in the axial direction to assist in lesion crossing. As described herein, the damping assembly 302, via the retention member 320 and the structure of the bore 306, as described herein, may damp transverse vibrations of the core wire 184 from the ultrasonic signal propagating therethrough. As a result, longitudinal vibrations of the tip member 186 may engage or cross the intravascular lesion.

Embodiments can be described with reference to the following numerical clauses:

1. A damping assembly for a core wire of an ultrasonic catheter assembly, the damping assembly comprising: a body for receiving the core wire, the body comprising a bore extending from a proximal end of the body, wherein the bore is defined by an interior surface of the body and comprises an insertion region at the proximal end and a compression region disposed distal to the insertion region; a plurality of compression members disposed within the compression region of the bore; and a retention member extending at least partially into the compression region to axially compress the plurality of compression members, wherein the interior surface of the body defining the insertion region of the bore corresponds in shape to at least a portion of an exterior surface of the retention member to facilitate insertion of the retention member into the bore.
2. The damping assembly of any preceding clause, wherein: the retention member comprises a first portion extending from a proximal end thereof and a second portion extending from a distal end thereof, and the first portion comprises a different cross-sectional shape than the second portion.

3. The damping assembly of any preceding clause, wherein the interior surface of the body defining the insertion region corresponds in shape to at least a portion of the first portion of the retention member.
4. The damping assembly of any preceding clause, wherein the first portion is substantially block-shaped and the second portion comprises a cylindrical-shaped peg extending distally from the first portion and contacting the plurality of compression members to axially compress the plurality of compression members.
5. The damping assembly of any preceding clause, wherein the compression region of the bore comprises a cylindrically-shaped cavity corresponding in size to the cylindrical-shaped peg.
6. The damping assembly of any preceding clause, wherein the insertion region of the bore comprises a plurality of grooves to receive corners of the first portion to facilitate insertion of the retention member into the bore.
7. The damping assembly of any preceding clause, wherein the bore further comprises a rotation region extending between the insertion region and the compression region, the rotation region permitting rotation of the retention member therein after insertion into the bore via the insertion region to retain the retention member in the bore.
8. The damping assembly of any preceding clause, wherein the insertion region comprises one or more insertion features corresponding in shape to one or more exterior surface components of the retention member to facilitate insertion of the retention member into the bore.
9. The damping assembly of any preceding clause, wherein: the insertion region comprises one or more locking features corresponding in shape to the one or more exterior surface components of the retention member, and the one or more locking features extend from a distal end of the insertion region and include ends that are disposed distally of the proximal end of the bore to retain the retention member at a desired position within the bore.
10. The damping assembly of any preceding clause, wherein the plurality of compression members comprise O-rings.
11. A system for modifying intravascular lesions comprising: an ultrasonic generator configured to generate an electric signal; an ultrasonic transducer communicatively coupled to the ultrasonic generator to receive the electric signal and generate vibrational energy; and a catheter assembly comprising: an ultrasonic connector coupling a core wire to the ultrasonic transducer to receive the vibrational energy therefrom; and a damping assembly comprising: a body receiving the core wire, the body comprising a bore defined by an interior surface of the body, wherein the bore comprises an insertion region at a proximal end of the body and a compression region disposed distal to the insertion region; a plurality of compression members disposed within the compression region of the bore; and a retention member extending at least partially into the compression region to axially compress the plurality of compression members, wherein the interior surface of the body defining the insertion region of the bore corresponds in shape to at least a portion of an exterior surface of the retention member to facilitate insertion of the retention member into the bore.
12. The system of any preceding clause, wherein: the retention member comprises a first portion extending from a proximal end thereof and a second portion extending from a distal end thereof, and the interior surface of the body defining the insertion region corresponds in shape to at least a portion of the first portion of the retention member.
13. The system of any preceding clause, wherein: the first portion is substantially block-shaped and the second portion comprises a cylindrical-shaped peg extending distally from the first portion and contacting the plurality of compression members to axially compress the plurality of compression members, and the compression region of the bore comprises a cylindrically-shaped cavity corresponding in size to the cylindrical-shaped peg.
14. The system of any preceding clause, wherein the insertion region of the bore comprises a plurality of grooves to receive corners of the first portion.
15. The system of any preceding clause, wherein the bore further comprises a rotation region extending between the insertion region and the compression region, the rotation region permitting rotation of the retention member therein after insertion into the bore via the insertion region to retain the retention member in the bore.
16. The system of any preceding clause, wherein the insertion region comprises one or more insertion features corresponding in shape to one or more exterior surface components of the retention member to facilitate insertion of the retention member into the bore.
17. The system of any preceding clause, wherein: the insertion region comprises one or more locking features corresponding in shape to the one or more exterior surface components of the retention member, and the one or more locking features extend from a distal end of the insertion region and include ends that are disposed distally of the proximal end of the bore to retain the retention member at a desired position within the bore.
18. A method for making a catheter assembly for modifying intravascular lesions, the method comprising: disposing a core wire within a body of a damping assembly, the body defining a bore; and inserting a retention member into the bore by aligning one or more exterior surface components of the retention member with one or more insertion features of the bore and compressing the plurality of compression members with the retention member such that the plurality of compression members damp vibrational energy in the core wire.
19. The method of any preceding clause, wherein inserting the retention member in the proximal end further comprises rotating the retention member in a rotation region of the damping assembly bore until the one or more exterior surface components of the retention member are aligned with one or more locking features in the bore.
20. The method of any preceding clause, wherein, once the one or more exterior surface components are aligned with the one or more locking features, the plurality of compression members force the one or more exterior surface components into the one or more locking features.

It should now be understood that embodiments of the present disclosure pertain to damping assemblies for ultrasonic systems comprising a bore through which a core wire extends, a plurality of compression members disposed in a compression region of the bore, and a retention member at least partially extending into the compression region to compress the plurality of compression members. The bore includes an insertion region shaped in a manner that at least partially corresponds in shape to the retention member to facilitate insertion of the retention member therein in a consistent manner. The bore may include a rotation region such that the retention member may be rotated to a position where the retention member is retained within the bore with a desired amount of compression of the compression members, to provide a desired amount of damping of particular vibration modes.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A damping assembly for a core wire of an ultrasonic catheter assembly, the damping assembly comprising:

a body for receiving the core wire, the body comprising a bore extending from a proximal end of the body, wherein the bore is defined by an interior surface of the body and comprises an insertion region at the proximal end and a compression region disposed distal to the insertion region;

a plurality of compression members disposed within the compression region of the bore; and a retention member extending at least partially into the compression region to axially compress the plurality of compression members, wherein the interior surface of the body defining the insertion region of the bore corresponds in shape to at least a portion of an exterior surface of the retention member to facilitate insertion of the retention member into the bore, wherein:

the insertion region comprises one or more locking features corresponding in shape to one or more exterior surface components of the retention member, and the one or more locking features extend from a distal end of the insertion region and include ends that are disposed distally of a proximal end of the bore to retain the retention member at a desired position within the bore.

2. The damping assembly of claim 1, wherein:

the retention member comprises a first portion extending from a proximal end thereof and a second portion extending from a distal end thereof, and the first portion comprises a different cross-sectional shape than the second portion.

3. The damping assembly of claim 2, wherein the interior surface of the body defining the insertion region corresponds in shape to at least a portion of the first portion of the retention member.

4. The damping assembly of claim 3, wherein the first portion is substantially block-shaped and the second portion comprises a cylindrical-shaped peg extending distally from the first portion and contacting the plurality of compression members to axially compress the plurality of compression members.

5. The damping assembly of claim 4, wherein the compression region of the bore comprises a cylindrically-shaped cavity corresponding in size to the cylindrical-shaped peg.

6. The damping assembly of claim 4, wherein the insertion region of the bore comprises a plurality of grooves to receive corners of the first portion to facilitate insertion of the retention member into the bore.

7. The damping assembly of claim 4, wherein the bore further comprises a rotation region extending between the insertion region and the compression region, the rotation region permitting rotation of the retention member therein after insertion into the bore via the insertion region to retain the retention member in the bore.

8. The damping assembly of claim 1, wherein the insertion region comprises one or more insertion features corresponding in shape to the one or more exterior surface components of the retention member to facilitate insertion of the retention member into the bore.

9. The damping assembly of claim 1, wherein the plurality of compression members comprise O-rings.

10. A system for modifying intravascular lesions comprising:

an ultrasonic generator configured to generate an electric signal;

an ultrasonic transducer communicatively coupled to the ultrasonic generator to receive the electric signal and generate vibrational energy; and a catheter assembly comprising:

an ultrasonic connector coupling a core wire to the ultrasonic transducer to receive the vibrational energy therefrom; and a damping assembly comprising:

a body receiving the core wire, the body comprising a bore defined by an interior surface of the body, wherein the bore comprises an insertion region at a proximal end of the body and a compression region disposed distal to the insertion region;

a plurality of compression members disposed within the compression region of the bore; and a retention member extending at least partially into the compression region to axially compress the plurality of compression members, wherein the interior surface of the body defining the insertion region of the bore corresponds in shape to at least a portion of an exterior surface of the retention member to facilitate insertion of the retention member into the bore, wherein:

the insertion region comprises one or more locking features corresponding in shape to one or more exterior surface components of the retention member, and the one or more locking features extend from a distal end of the insertion region and include ends that are disposed distally of a proximal end of the bore to retain the retention member at a desired position within the bore.

11. The system of claim 10, wherein:

the retention member comprises a first portion extending from a proximal end thereof and a second portion extending from a distal end thereof, and the interior surface of the body defining the insertion region corresponds in shape to at least a portion of the first portion of the retention member.

12. The system of claim 11, wherein:

the first portion is substantially block-shaped and the second portion comprises a cylindrical-shaped peg extending distally from the first portion and contacting the plurality of compression members to axially compress the plurality of compression members, and the compression region of the bore comprises a cylindrically-shaped cavity corresponding in size to the cylindrical-shaped peg.

13. The system of claim 12, wherein the insertion region of the bore comprises a plurality of grooves to receive corners of the first portion.

14. The system of claim 12, wherein the bore further comprises a rotation region extending between the insertion region and the compression region, the rotation region permitting rotation of the retention member therein after insertion into the bore via the insertion region to retain the retention member in the bore.

15. The system of claim 10, wherein the insertion region comprises one or more insertion features corresponding in shape to the one or more exterior surface components of the retention member to facilitate insertion of the retention member into the bore.

16. A method for making a catheter assembly for modifying intravascular lesions, the method comprising:

disposing a core wire within a body of a damping assembly, the body defining a bore;

disposing a plurality of compression members in the bore around the core wire;

inserting a retention member into the bore by aligning one or more exterior surface components of the retention member with one or more insertion features of the bore;

rotating the retention member in a rotation region of the damping assembly bore until the one or more exterior surface components of the retention member are aligned with one or more locking features in the bore; and compressing the plurality of compression members with the retention member such that the plurality of compression members damp vibrational energy in the core wire.

17. The method of claim 16, wherein, once the one or more exterior surface components are aligned with the one or more locking features, the plurality of compression members force the one or more exterior surface components into the one or more locking features.

* * * * *